US012191005B2

(12) United States Patent
Wimberger-Friedl et al.

(10) Patent No.: US 12,191,005 B2
(45) Date of Patent: Jan. 7, 2025

(54) RADIOLOGY-BASED RISK ASSESSMENT FOR BIOPSY-BASED SCORES

(71) Applicant: KONINKLIJKE PHILIPS N.V., Eindhoven (NL)

(72) Inventors: Reinhold Wimberger-Friedl, Waalre (NL); Pedro Jorge Da Silva Rodrigues, Veldhoven (NL); Vanda Lucia De Carvalho Vittorino De Almeida, Veldhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 426 days.

(21) Appl. No.: 17/625,105

(22) PCT Filed: Jul. 22, 2020

(86) PCT No.: PCT/EP2020/070604
§ 371 (c)(1),
(2) Date: Jan. 6, 2022

(87) PCT Pub. No.: WO2021/013858
PCT Pub. Date: Jan. 28, 2021

(65) Prior Publication Data
US 2022/0262465 A1 Aug. 18, 2022

(30) Foreign Application Priority Data
Jul. 22, 2019 (EP) .................................... 19187572

(51) Int. Cl.
*G16H 50/20* (2018.01)
*G16H 10/40* (2018.01)
*G16H 30/40* (2018.01)

(52) U.S. Cl.
CPC ............. *G16H 10/40* (2018.01); *G16H 30/40* (2018.01); *G16H 50/20* (2018.01);
(Continued)

(58) Field of Classification Search
None
See application file for complete search history.

(56) References Cited

U.S. PATENT DOCUMENTS 9,360,481 B2 * 6/2016 Di Scala ................. C07K 16/30
9,922,433 B2 * 3/2018 Schieke ................. G06T 7/0012
(Continued)

FOREIGN PATENT DOCUMENTS

| WO | 20160160538 A1 | 10/2016 |
| WO | 20180175501 A1 | 9/2018 |
| WO | 2019012147 A1 | 1/2019 |

OTHER PUBLICATIONS

Niemeijer et al "Whole Body PD-1 and PD-L1 Positron Emission Tomography in Patients With Non-Small Cell Lung Cancer" Naure Communications 2018.
(Continued)

*Primary Examiner* — Idowu O Osifade (57) ABSTRACT

A computer-implemented method for determining tumor heterogeneity is provided. Embodiments of the method involve analyzing a radiological image of a tumor to calculate a value indicative of tumor activity at each of a plurality of locations in the tumor; determining whether each calculated value is above a predetermined threshold; and calculating a heterogeneity score for the tumor; wherein the heterogeneity score is calculated based on a volume fraction of the tumor having a value indicative of tumor activity above the predetermined threshold. Also provided are associated systems and computer program products.

15 Claims, 4 Drawing Sheets

(52) U.S. Cl.
CPC ............... *G06T 2207/10081* (2013.01); *G06T 2207/10088* (2013.01); *G06T 2207/10104* (2013.01)

(56) References Cited

U.S. PATENT DOCUMENTS

| | | | | |
|---|---|---|---|---|
| 2007/0014454 | A1* | 1/2007 | Sawyer | A61N 5/1049 |
| | | | | 382/128 |
| 2014/0314292 | A1 | 10/2014 | Kamen et al. | |
| 2016/0203599 | A1* | 7/2016 | Gillies | A61B 6/5211 |
| | | | | 382/132 |
| 2018/0036442 | A1* | 2/2018 | Lahoutte | A61K 51/1078 |
| 2018/0369611 | A1* | 12/2018 | Owens | A61N 5/1071 |

OTHER PUBLICATIONS

Takada et al, "Metabolic characteristics of programmed cell death-ligand 1—expressing lung cancer on 18F fluorodeoxyglucose positron emission tomography/computed tomography", Cancer Medicine 2017; 6(11):2552-2561, 10.1002/cam4.1215.

Kinahan et al "PET/CT Standardized Uptake Values (SUVs) in Clinical Practice and Assessing Response to Therapy" Semin Ultrasound CT MR, Dec. 2010 vol. 31(6) p. 496-505.

Zhou et al "Relationship Between Maximal Standardization Uptake Vaule on FDG-PET and PD-L1 Expression in Clear Cell Renal Cell Carcinoma" Eur J. Nucl Med Mol .Imaging 45 Suppl s441 EP-0367.

International Search Report and Written Opinion from PCT/EP2020/070604 mailed Jan. 28, 2021.

* cited by examiner

RADIOLOGY-BASED RISK ASSESSMENT FOR BIOPSY-BASED SCORES

CROSS REFERENCE TO RELATED APPLICATIONS

This application is a U.S. national phase application of International Application No. PCT/EP2020/070604 filed Jul. 22, 2020, which claims the benefit of EP application Ser. No. 19187572.3 filed Jul. 22, 2019 and is incorporated herein by reference.

FIELD OF THE INVENTION

Embodiments described herein generally relate to methods, systems and computer program products for determining tumor heterogeneity. In particular aspects, the invention relates to computer-implemented methods for determining representativeness of pathology scores obtained from processing of biopsy samples of tumor tissue, for instance scores indicative of the expression of programmed death 1 receptor and its ligand (PD-1/PD-L1). The methods are particularly applicable to determining whether pathology scores obtained from potentially heterogeneous tumors are likely to be inaccurate. The outputs of such methods are useful in clinical decision making, e.g. for determining further diagnostic and/or therapeutic steps in the treatment of cancer.

BACKGROUND OF THE INVENTION

With the introduction of checkpoint inhibition immunotherapies (CIT), treatments that modulate the immune system, have become an important class of therapy for cancer, with FDA approvals for many cancer types even in first line treatment. These therapies can achieve durable responses in late stage patients. However, the percentage of responders is, depending on the cancer type, only between 15 and 30% for monotherapy. The basic mechanism of CIT is the activation of cytotoxic T cells which are able to recognize the tumor as foreign. By blocking the checkpoint molecules on the target cells the effector function can be engaged and tumor cells can be killed by the infiltrating T cells.

The clinically most important checkpoint is the programmed death 1 receptor and ligand (PD-1/PD-L1). Overexpression of the PD-L1 molecule on tumor cells is used as biomarker for patient selection in first line therapy for various cancer, such as non-small cell lung carcinoma (NSCLC).

Most patients with lung cancer are diagnosed at an advanced stage, and diagnosis is based on a small biopsy or cytology specimen. In the advanced cancer setting surgery is generally not applicable. There are several techniques available for obtaining a biopsy sample in lung cancer, including bronchoscopy, ultrasound-guided bronchoscopy, mediastinoscopy, transthoracic needle aspiration, thoracentesis, and medical thoracoscopy. All of those have limitations regarding tissue yields and their use depends very much on the location of the lesion and its accessibility. For lung cancer that is a major challenge. In the best case, a transthoracic needle aspiration is performed with core-needle of 20- to 22-gauge, that usually contain approximately 500 cells per core biopsy. This material is then paraffin embedded and cut in thin sections for microscopic analysis.

Treatment selection in CIT therefore typically involves determining PD-L1 expression on tumor cells in a biopsy sample obtained from the patient using such techniques. However, it has become clear that PD-L1 expression is not a good predictor of response of a patient. One reason is the strong spatial heterogeneity of the expression of this biomarker which limits the validity of a determination on a small biopsy at a single time point.

Tumors are composed of different cell and tissue types. Cancer cells at different locations inside the tumor can vary in their genetic makeup, activity and environment-dependent signalling behaviour. It has been noted that in particular the relevant PD-L1 expression can vary largely within a single lesion as well as between lesions of the same patient. For the determination of PD-L1 expression by immunohistochemistry in general only a biopsy is available. The score obtained from the biopsy might not reflect the average properties of the tumor. In this way a negative result on the biopsy might turn out to be a false negative as other parts of the tumor could be positive.

Currently, there is no way of estimating the chances of having a non-representative biopsy with a potentially incorrect pathological assessment. The PD-L1 score is an important element in the treatment decision. There is therefore a need for a method to determine tumor heterogeneity, which can be used to predict how representative a biopsy sample obtained the tumor is likely to be. In particular, there is a need for a method capable of predicting the likelihood of obtaining a biopsy specimen for pathological assessment which is representative of the tumor with respect to e.g. PD-L1 expression.

SUMMARY OF THE INVENTION

The object of the present invention is solved by the subject matter of the independent claims where further embodiments are incorporated in the dependent claims. It should be noted that the following described aspects of the invention apply equally to the method for determining tumor heterogeneity, to the system and to the computer program product.

In embodiments of the present invention, a tumor heterogeneity score is calculated based on radiology image analysis, e.g. using positron emission tomography (PET). The radiology image analysis can be used to indicate a risk of obtaining a non-representative result from a pathological analysis of a biopsy sample. In particular, using the present method the heterogeneity score obtained from radiology image analysis can be compared with a pathology score obtained from analyzing a biopsy sample. By comparing the heterogeneity score with the pathology score it is possible to predict the representativeness of the pathology score for the tumor as a whole. For instance in some embodiments, the method may predict that the biopsy-based (pathology) score is unrepresentative and/or inaccurate because of a local variation in the tumor at the biopsy site. This can have important implications for therapy, e.g. by identifying false negative results in the pathology scores and indicating a need for further samples/testing.

For example, in one embodiment FDG-PET/CT image analysis is used to indicate the potential heterogeneity of PD-L1 expression in a biopsy sample, and thus the probability of obtaining an incorrect/unrepresentative PD-L1 score on the biopsy. In another embodiment the radiology image analysis may be used for guiding the taking of biopsy samples.

Thus in one embodiment, the present invention provides a computer-implemented method for determining tumor heterogeneity, the method comprising: analyzing a radiological image of a tumor to calculate a value indicative of tumor activity at each of a plurality of locations in the tumor; determining whether each calculated value is above a predetermined threshold; and calculating a heterogeneity score for the tumor; wherein the heterogeneity score is calculated based on a volume fraction of the tumor having a value indicative of tumor activity above the predetermined threshold.

In one embodiment, the method further comprises calculating a probability of a biopsy sample obtained from the tumor having a value of tumor activity above the predetermined threshold, wherein the probability is calculated based on the heterogeneity score and a volume of the biopsy sample.

In another embodiment, the method further comprises: analysing a microscopy image of a biopsy sample of the tumor to determine a value of a biological parameter associated with the tumor; and determining a likelihood of the value of the biological parameter being representative of the tumor, wherein the likelihood is calculated based on the heterogeneity score and/or the probability.

In some embodiments, the radiological image is obtained by positron emission tomography (PET), magnetic resonance imaging (MRI), computerized tomography (CT) and/or single-photon emission computed tomography (SPECT).

In one embodiment, the value indicative of tumor activity in the tissue is a standard uptake value (SUV), e.g. obtained by PET. For example, the value indicative of tumor activity (e.g. SUV) may be obtained by PET imaging using (18-F) fluorodeoxyglucose (FDG).

In one embodiment, the biological parameter comprises an expression level of programmed death-ligand 1 (PD-L1) on tumor cells.

In one embodiment, the method further comprises calculating a contour plot showing regions of the tumor having equal values of tumor activity. Preferably at least one contour in the contour plot corresponds to the predetermined threshold of tumor activity. In some embodiments, the contour plot may comprise a plurality of contours, each contour corresponding to a different predetermined threshold of tumor activity. In some embodiments, each contour (and each predetermined threshold of tumor activity) may correlate to a clinically relevant threshold of the biological parameter, e.g. a different percentage of tumor cells positive for PD-L1 expression (tumor proportion score or TPS), such as e.g. 1% or 50%.

In one embodiment, the method further comprises indicating to a user a region of the tumor having tumor activity above a predetermined threshold from which a biopsy sample is to be extracted.

In one embodiment, the volume fraction of the tumor is determined based on a minimum connected volume with a value above the predetermined threshold.

In one embodiment, the value indicative of tumor activity is indicative of metabolic activity, hypoxia and/or proliferation in the tumor.

In one embodiment, each value indicative of tumor activity is determined for a volume element within the tumor, and an average value for the volume element is compared to the predetermined threshold. In another embodiment, each value indicative of tumor activity is determined for a volume element within the tumor, and a maximum value for the volume element is compared to the predetermined threshold.

In one embodiment, the value of tumor activity (e.g. obtained from the radiological image) correlates with the value of the biological parameter (e.g. obtained from a microscopy image). Preferably the predetermined threshold of tumor activity is correlated with a clinically relevant threshold of a biological parameter associated with the tumor. For instance, in one embodiment the biological parameter is a percentage of tumor cells positive for PD-L1 expression (tumor proportion score or TPS). The clinically relevant threshold may be e.g. a value of TPS indicative of suitability for checkpoint inhibitor therapy (or e.g. a specific modality thereof, such as checkpoint inhibitor therapy in combination with chemotherapy).

In one embodiment, the heterogeneity score is compared with the value of the biological parameter. For instance, a discordance between the heterogeneity score and the value of the biological parameter may be indicative that the value of the biological parameter is unrepresentative. In particular, if the value of the biological parameter is below the clinically relevant threshold, the heterogeneity score may indicate that a significant volume fraction of the tumor has an activity that is above the corresponding predetermined threshold. In such an embodiment, taking a further biopsy sample may be recommended.

In a further aspect, the present invention provides a system for determining tumor heterogeneity, the system comprising: an interface for receiving a radiological image of a tumor; a memory; and a processor configured to execute instructions stored on the memory to: (a) analyze the radiological image of the tumor to calculate a value indicative of tumor activity at each of a plurality of locations in the tumor; (b) determine whether each calculated value is above a predetermined threshold; and (c) calculate a heterogeneity score for the tumor; wherein the heterogeneity score is calculated based on a volume fraction of the tumor having a value indicative of tumor activity above the predetermined threshold.

In a further aspect, the present invention provides a computer program product comprising a non-transitory computer readable medium, the computer readable medium having computer readable code embodied therein, the computer readable code being configured such that, on execution by a suitable computer or processor, the computer or processor is caused to perform the method as described above.

BRIEF DESCRIPTION OF THE DRAWINGS

Exemplary embodiments of the invention will now be described with reference to the following drawings wherein.

DETAILED DESCRIPTION OF EMBODIMENTS

Pathology information is essential for diagnosing, staging and subtyping of cancer. Often only a small core or needle biopsy sample is available. Since tumor properties display spatial heterogeneity, there is significant risk of having a non-representative diagnostic result. Describe herein in one embodiment is a method using radiology image analysis to indicate the risk of having a non-representative result from the pathological analysis of the biopsy. As one embodiment we describe the use of FDG-PET/CT image analysis to indicate the potential heterogeneity of the PD-L1 expression and the chances of obtaining an incorrect PD-L1 score on the biopsy. Another embodiment describes the use of such an analysis for guiding biopsy taking.

Various embodiments are described more fully below with reference to the accompanying drawings, which form a part hereof, and which show specific exemplary embodiments. However, the concepts of the present disclosure may be implemented in many different forms and should not be construed as limited to the embodiments set forth herein; rather, these embodiments are provided as part of a thorough and complete disclosure, to fully convey the scope of the concepts, techniques and implementations of the present disclosure to those skilled in the art. Embodiments may be practiced as methods, systems or devices. Accordingly, embodiments may take the form of a hardware implementation, an entirely software implementation or an implementation combining software and hardware aspects. The following detailed description is, therefore, not to be taken in a limiting sense.

Reference in the specification to "one embodiment" or to "an embodiment" means that a particular feature, structure, or characteristic described in connection with the embodiments is included in at least one example implementation or technique in accordance with the present disclosure. The appearances of the phrase "in one embodiment" in various places in the specification are not necessarily all referring to the same embodiment.

Unless specifically stated otherwise as apparent from the following discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices. Portions of the present disclosure include processes and instructions that may be embodied in software, firmware or hardware, and when embodied in software, may be downloaded to reside on and be operated from different platforms used by a variety of operating systems. The invention may take form in various components and arrangements of components, and in various process operations and arrangements of process operations.

The present disclosure also relates to an apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, such as, but not limited to, any type of disk including floppy disks, optical disks, CD-ROMs, magnetic-optical disks, read-only memories (ROMs), random access memories (RAMS), EPROMs, EEPROMs, magnetic or optical cards, application specific integrated circuits (ASICs), or any type of media suitable for storing electronic instructions, and each may be coupled to a computer system bus. Furthermore, the computers referred to in the specification may include a single processor or may be architectures employing multiple processor designs for increased computing capability.

The processes and displays presented herein are not inherently related to any particular computer or other apparatus. Various general-purpose systems may also be used with programs in accordance with the teachings herein, or it may prove convenient to construct more specialized apparatus to perform one or more method steps. The structure for a variety of these systems is discussed in the description below. In addition, any particular programming language that is sufficient for achieving the techniques and implementations of the present disclosure may be used. A variety of programming languages may be used to implement the present disclosure as discussed herein.

In addition, the language used in the specification has been principally selected for readability and instructional purposes and may not have been selected to delineate or circumscribe the disclosed subject matter. Accordingly, the present disclosure is intended to be illustrative, and not limiting, of the scope of the concepts discussed herein. Numerous additional advantages and benefits will become apparent to those of ordinary skill in the art upon reading the following detailed description.

Figure 1:
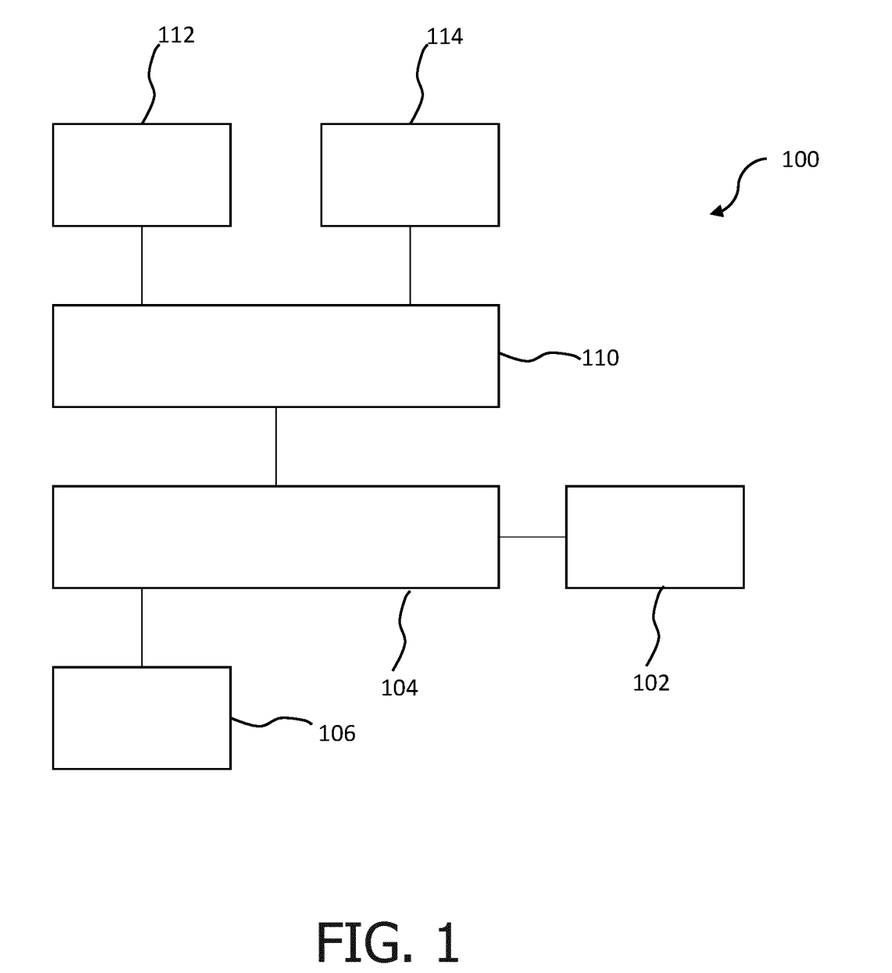
FIG. 1 shows a systematic block diagram of a computerized system for determining tumor heterogeneity.

FIG. 1 illustrates a system 100 for determining tumor heterogeneity in accordance with one embodiment.

The system 100 may include a user input/output (I/O) device 102 and a processor 104 executing instructions stored on memory 106. The processor 104 may be in communication with or otherwise include an interface 110 for receiving imaging data from image data sources 112 and 114. For instance image data source 112 may comprise a radiological imaging system such as a PET scanner, whereas image data source 114 may comprise a microscopy imaging system, such as a digital microscope.

The I/O device 102 may be any suitable device that can receive commands from an operator and output radiological and imaging data and scores associated therein. The I/O device 102 may be configured as, for example but without limitation, a personal computer, a tablet, laptop, mobile device, or the like.

The processor 104 may be any specifically configured processor or hardware device capable of executing instructions stored on memory 106 to process radiological and optionally microscopy imaging data in order to determine quantitative values therefrom. The processor 104 may include a microprocessor, a field programmable gate array (FPGA), application-specific integrated circuit (ASIC), or other similar device. In some embodiments, such as those relying on one or more ASICs, the functionality described as being provided in part via software may instead be hardwired into the operation of the ASICs, and as such, any associated software may be omitted.

The memory 106 may be L1, L2, L3 cache or RAM memory configurations. The memory 106 may include non-volatile memory such as flash memory, EPROM, EEPROM, ROM, and PROM, or volatile memory such as static or dynamic RAM, as discussed above. The exact configuration/type of memory 106 may of course vary as long as instructions for analyzing radiological and optionally microscopy imaging data can be executed by the processor 104.

The interface 110 may receive radiological imaging data from the data source 112, and optionally microscopy imaging data from data source 114. The interface 110 may then communicate the received data to the processor 104 for analysis. The radiological and microcopy imaging data is typically in the form of digital images of a tissue of interest within the subject. The radiological image typically shows tumor activity at various locations within the tumor. The radiological image may be e.g. obtained by PET analysis, and standard data processing techniques may be employed to convert the raw data to an image indicative of tumor activity. In addition, corrections may be employed to take e.g. contrast agent concentration and tracer decay into account. The microscopy imaging data may, for example, show expression of a tumor marker of other protein of interest within the tumor.

The processor 104 is configured to calculate a value indicative of tumor activity at each of a plurality of locations in the radiological image, and to determine whether each calculated value is above a predetermined threshold. Typically the predetermined threshold is derived from a correlation of tumor activity with a biological parameter of interest. For instance, the predetermined threshold (for tumor activity) may correspond to a particular clinical threshold for the biological parameter that is indicative of a diagnosis or treatment decision. The processor 104 then calculates a heterogeneity score for the tumor, based on a volume fraction of the tumor having a tumor activity value above the predetermined threshold.

In some embodiments, the processor 104 may be further configured to calculate a representativeness score for a biopsy sample obtained from the tumor. The representativeness score may correspond to a probability that a biopsy sample obtained from the tumor has a (e.g. mean or average) value of tumor activity above the predetermined threshold. Since tumor activity may correlate with the biological parameter of interest, the representativeness score may also correspond to a probability that a biopsy sample obtained from the tumor has a value of the biological parameter above a clinically relevant threshold. The processor may be configured to calculate this probability based on the heterogeneity score and a volume of the biopsy sample.

In some embodiments, processor 104 may analyze the microscopy image to determine a biological parameter associated with the tumor, e.g. an expression level of a protein of interest in the tissue. The processor may then determine a likelihood or probability of the value of biological parameter being representative of the tumor, based on the heterogeneity score, the predetermined threshold and/or the probability. In alternative embodiments, the analysis of the microscopy image may be performed manually, e.g. by a pathologist or other clinician. A clinician may also make a manual determination of the probability of the value of the biological parameter being representative of the tumor.

After analysis of the received data, the processor 104 may output e.g. the heterogeneity score, the representativeness score and/or the probability to the I/O device 102 or another display unit. In some embodiments, the output may include a diagnostic and/or treatment recommendation, e.g. and indication that a further biopsy sample should be taken and analyzed.

Figure 2:
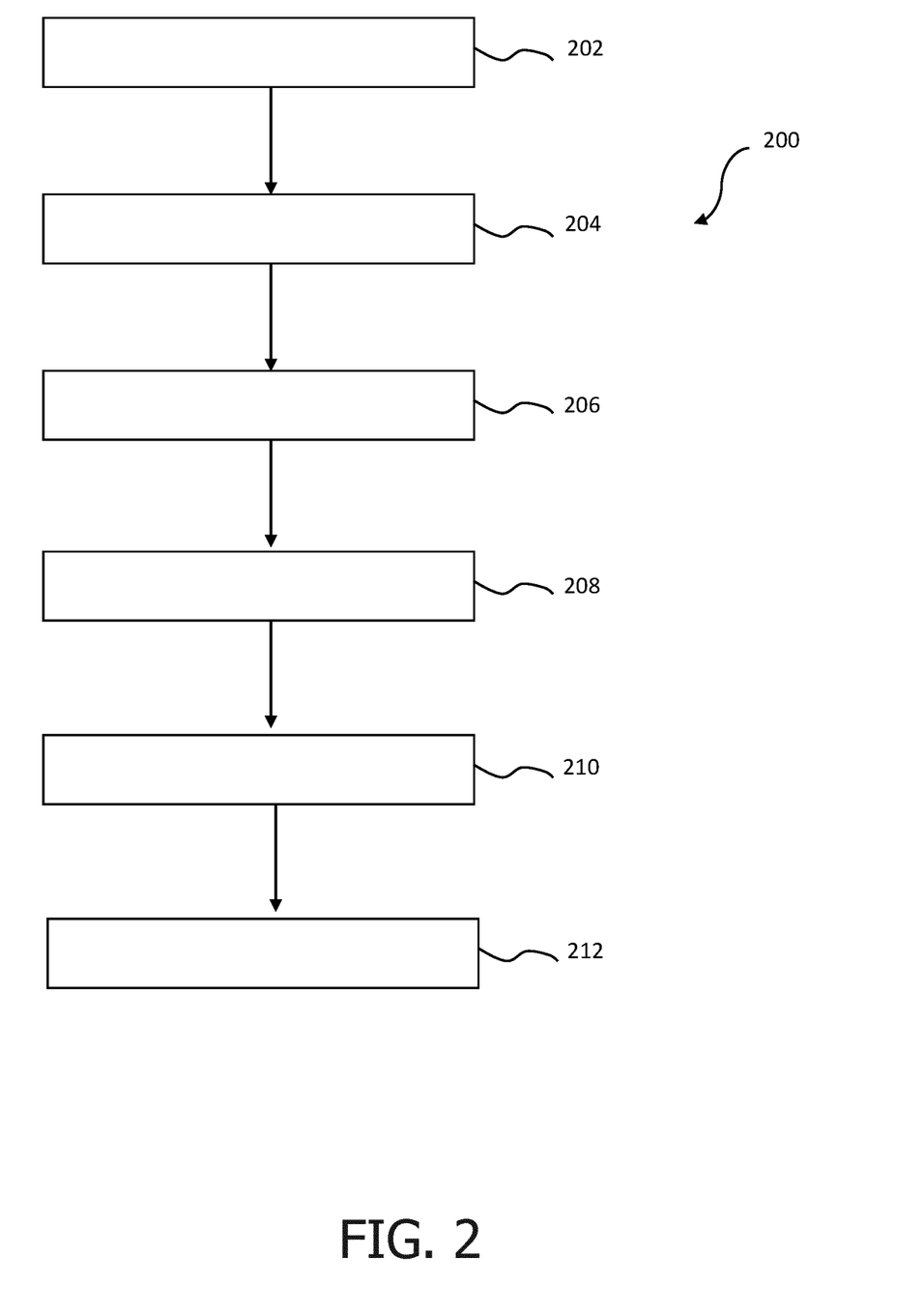
FIG. 2 shows a flow chart of a method for determining tumor heterogeneity according to the present invention.

FIG. 2 depicts a flowchart of a method 200 for determining tumor heterogeneity using the system of FIG. 1 in accordance with one embodiment. Step 202 involves analyzing a radiological image of a tumor to calculate a value indicative of tumor activity at each of a plurality of locations in the tumor. "Image" as used herein should be construed broadly, to include not only a whole array of image signals but, in an extreme case, a single image signal for a single voxel position or a selection of such image signals for a sub-set of voxel positions in the whole field of view.

The value indicative of tumor activity may be, for example, a standard uptake value (SUV). For instance, the SUV may be obtained by PET imaging using (18-F) fluorodeoxyglucose (FDG). In some embodiments, the SUV may be calculated as an average or mean value over a defined volume at each of the plurality of locations in the tissue. In such embodiments, each defined volume of tissue in the sample is represented by a single value indicative of metabolic activity. In alternative embodiments, the radiological image may be analyzed to calculate SUV values at each single voxel position in the tissue. In these embodiments, the SUV values at various locations in the tissue may be represented visually by an image showing the distribution of values (e.g. SUVs) across the tissue.

The radiological image may be received by the interface 110 from the radiological imaging system 112. A processor such as the processor 104 of FIG. 1 may receive these images from the interface 110 of FIG. 1. In alternative embodiments, the radiological image may be transmitted to the interface 110 and/or processor 104 by the I/O device 102, e.g. where the image is stored in another location after image acquisition by imaging systems.

Step 204 involves determining whether each calculated value (e.g. the SUV at each location) is above a predetermined threshold.

Step 206 involves calculating a heterogeneity score for the tumor. The heterogeneity score typically corresponds to a volume fraction of the tumor that has a tumor activity value above the predetermined threshold. The heterogeneity score may thus be obtained e.g. by dividing the number of calculated values (of the SUV) determined to be above the threshold by the total number of calculated values. In the case where an SUV is calculated for each voxel, this corresponds to the number of voxels above the threshold divided by the total number of voxels within a delineated lesion volume.

In some embodiments, additional step 208 may comprise calculating a representativeness score for a biopsy sample to be taken from the tumor. The representativeness score may correspond to a probability that the biopsy sample has a (e.g. mean) value of tumor activity above the predetermined threshold and/or a probability that the biopsy sample has a value of the biological parameter that is above a clinically relevant threshold. This probability may be calculated based on the heterogeneity score and a known volume of the biopsy sample. For instance, if a biopsy sample has a relatively small volume compared to the tumor as a whole, the representativeness score will be similar to the heterogeneity score. As the volume of the biopsy sample increases, the representativeness score decreases, since there is an increasing risk of including volume elements below threshold that would decrease the mean value of tumor activity below the threshold.

The method may further optionally comprise step 210, in which a microscopy image of a biopsy sample is analyzed to determine a value of a biological parameter associated with the tumor. For instance, the processor 104 may use an algorithm suitable for analysis of digital microscopy images to identify stained objects and/or an overall level of staining within the tissue, e.g. to identify an expression level of a protein which has been stained in the image by immunohistochemical processing of the biopsy sample. In one embodiment, the processor analyses the image to determine an expression level of PD-L1 on tumor cells in the tissue. The output of this analysis may be a continuous variable (e.g. a percentage of tumor cells positive for PD-L1) or a binary result (e.g. a positive/negative score for PD-L1 based on whether expression is above or below a defined cut-off level).

The method may further optionally comprise step 212, in which the processor determines a likelihood or probability that the value of the biological parameter is representative of the tumor. This likelihood may e.g. be determined from the representativeness score, since the probability of the biopsy sample being obtained from a region of the tumor having a tumor activity above the threshold is directly linked to the likelihood that the value of the biological parameter is representative of the tumor as a whole. Alternatively, the likelihood may be determined from the heterogeneity score, since this is linked to the representativeness score depending on the volume of the biopsy sample.

The output of the method may be e.g. the heterogeneity score, the representativeness score and/or an indication of the likelihood that the value of the biological parameter is representative of the tumor. One or more of these results may be outputted via the I/O device 102 or a display.

In one embodiment, one or more radiology-derived features may be compared with one or more pathology-derived features in order to check for concordance. For instance the value of the biological parameter (obtained from analysis of the microscopy image) may be compared with the heterogeneity score (obtained from analysis of the radiological image). If a significant volume fraction of the tumor is found to have a tumor activity above threshold (as indicated by the heterogeneity score), it might be expected to obtain a value of the biological parameter (e.g. PD-L1 expression) above a clinically relevant threshold as well. If that is not the case, this can be flagged as an unexpected (or discordant) result and indicated to the clinician.

The present method is directed in general to determining tumor heterogeneity, and involves calculation of a heterogeneity score for the tumor. By "heterogeneity score" it is meant that the score is linked to spatial variability in the properties of the tumor, e.g. in terms of functional activity and/or expression of one or more tumor markers. In embodiments of the present invention, the heterogeneity score is represented by a volume fraction of the tumor having a value indicative of tumor activity above a predetermined threshold. Thus a high value of the score may be indicative of relatively low heterogeneity (i.e. tumor activity is relatively high and uniform across the entire tumor volume). Conversely a low value of the score may be indicative of relatively high heterogeneity (i.e. a significant portion of the tumor volume shows relatively low activity compared to other regions of high activity). Thus the heterogeneity score may e.g. be inversely proportional to variability of tumor activity. In some embodiments, the heterogeneity score may thus alternatively be referred to as e.g. a tumor activity score, a tumor activity consistency score or an above-threshold volume fraction tumor activity score.

The radiological image (e.g. as analyzed in step 202 shown in FIG. 2) may be obtained by any suitable radiological imaging method, for example, by positron emission tomography (PET), computerized tomography (CT), magnetic resonance imaging (MRI) and/or single-photon emission computed tomography (SPECT). Typically, the image is a PET image.

The value indicative of tumor activity in the tissue, e.g. determined by PET imaging, may be e.g. a measure of metabolic activity of the tumor. "Metabolic activity" as used herein includes chemically transforming (or processing) certain chemical compounds ("metabolites") by a cell of the human or animal body. One important but non-limiting example is the transformation of glucose to obtain energy.

The TCA cycle is a critical metabolic pathway that allows mammalian cells to utilize glucose, amino acids, and fatty acids. The entry of these fuels into the cycle is carefully regulated to efficiently fulfil the cell's bioenergetics, biosynthetic, and redox balance requirements. The cancer cells, in comparison with normal cells, exhibit distinctive physiopathology, including: (a) autonomous mechanisms of cell growth, (b) divergence from the factors involved in growth inhibition, (c) evasion from anoikis, immune-surveillance and apoptosis, (d) evolutionary regulation of growth, (e) invasiveness and metastatic colonization.

To carry out replicative division, a cell must duplicate its genome, proteins and lipids and assemble these elements into daughter cells. The increased rate of cell division in cancer requires metabolic pathways to be redesigned, giving rise to the tumor cell metabolism. Reprogramming of glucose metabolism is a key event in tumorigenesis. Tumor cells undergo a metabolic switch from oxidative phosphorylation (OXPHOS) to glycolysis in which a molecule of glucose is degraded to two molecules of pyruvate. Depending on the supply of oxygen for the cells, pyruvate is either reduced to lactate in the absence of oxygen via an anaerobic glycolysis pathway, or oxidized to yield acetyl-coenzyme A in the presence of oxygen and then oxidized completely to $CO_2$ and $H_2O$ via citric acid cycle. The majority of tumor cells depend on high rates of glycolysis for growth and survival, even when there is sufficient oxygen. This type of aerobic glycolysis is called the Warburg effect.

To support this continuous cell proliferation, the biosynthetic capabilities of tumor cells are increased, including fatty acid and nucleotide synthesis. In contrast, b-oxidation of fatty acids is suppressed and futile cycles are minimized. These changes increase the metabolic autonomy of the transformed cells, allowing them to acquire an enhanced anabolic phenotype. Thus metabolic activity in the tissue can be used as a marker of tumor activity.

PET scanning with the tracer fluorine-18 (18-F) fluoro-deoxyglucose (FDG), called FDG-PET, is widely used in clinical oncology. This tracer is a glucose analog that is taken up by glucose-using cells and phosphorylated by hexokinase (whose mitochondrial form is greatly elevated in rapidly growing malignant tumors). The typical administered $^{18}$F-FDG activity used in an oncological scan is in the range of 200-450 MBq. Because the oxygen atom that is replaced by F-18 to generate FDG is required for the next step in glucose metabolism in all cells, no further reactions occur in FDG. Furthermore, most tissues (with the notable exception of liver and kidneys) cannot remove the phosphate added by hexokinase. This means that FDG is trapped in any cell that takes it up, until it decays, since phosphorylated sugars, due to their electrical charge, cannot exit from the cell. This results in intense radiolabelling of tissues with high glucose uptake, such as the brain, the myocardium, the liver, and most cancers. As a result, FDG-PET can be used for diagnosis, staging, treatment planning and monitoring treatment of cancers, particularly in Hodgkin's lymphoma, non-Hodgkin lymphoma, breast, melanoma, and lung cancer. The analysis of PET images is well established and signal intensities, as expressed in Standard Uptake Values (SUV, SUVmax) are used for staging and prognosis.

Thus, in one embodiment the value indicative of tumor activity is an SUV, e.g. the radiological image is obtained by PET imaging using $^{18}$F-FDG. Other suitable measures derived from the PET images which may be used to indicate tumor activity include e.g. SUVmax, SUVmean, Metabolic Tumor Volume (MTV), Total Lesion Glycolysis (TLG), or other, high-order, so-called radiomics features. See e.g. Paul E Kinahan et al in "PET/CT Standardized Uptake Values (SUVs) in Clinical Practice and Assessing Response to Therapy", Semin Ultrasound CT MR, December 2010 December, vol 31(6), pp 496-505.

In other embodiments, further biological parameters may be used to indicate tumor activity, as an alternative to parameters indicative of metabolic activity. In general, various functional and/or anatomic parameters can be assessed using radiological imaging methods in order to determine tumor activity. For instance, specific PET tracers may be used to determine tumor proliferation and/or hypoxia as a marker of tumor activity. In one embodiment, a value indicative of tumor cell proliferation in the tissue may be determined from an image obtained using 18F-FLT PET imaging. In another embodiment, values indicative of tumor cell hypoxia may be calculated from an image obtained with an appropriate tracer (e.g. using 18F-FMISO PET imaging).

In further embodiments, the marker indicative of tumor activity may be e.g. PD-L1 expression as determined in the tumor using radiological imaging. For instance, PD-L1 expression in the tissue may be determined from a PET image obtained using an anti-PD-L1 antibody PET tracer (e.g. 89Zr-atezolizumab, 18F-BMS-986192). In some such embodiments, the heterogeneity score may additionally be comparable to a pathology score for the expression of a biological parameter such as PD-L1 which is measured in a biopsy sample from the tumor. In other words, the radiology (e.g. PET) score for PD-L1 expression can be compared to the pathology score for PD-L1 expression. A significant disparity between the two values would be indicative that the pathology-derived value is potentially incorrect/unrepresentative and that a further biopsy should be taken and analysed.

In one embodiment, the value indicative of tumor activity may be calculated by analyzing a combination of images obtained by PET (e.g. providing metabolic activity) and contrast-enhanced perfusion CT (e.g. providing information on angiogenesis and blood-flow characteristics in tumors). In specific embodiments, CT perfusion data (e.g. blood flow (BF), blood volume (BV) and Mean Transit Time (MTT)) is obtained by an analysis of the time-contrast enhancement curve. In one embodiment, perfusion status of the tissue can also be derived from MR images.

The methods described herein involve in some embodiments (e.g. in step 210 shown in FIG. 2) a step of analyzing a microscopy image of the tissue. The microscopy image is typically a digital light microscopy image, e.g. obtained by a digital microscope. The microscopy image typically shows a portion of the same tissue which is the subject of the radiological image, e.g. the microscopy image is of a tissue specimen obtained from a biopsy or resected tissue sample taken from a tumor in the subject who has been imaged using e.g. PET.

The tissue specimen (e.g. obtained by biopsy or resection from a subject) can be prepared using known techniques for light microscopy analysis and imaging. For instance, haemotoxylin and eosin (H&E) staining of paraffin-embedded sections is the default technology to visualize tissue on a glass slide for pathology analysis. Immunohistochemistry (IHC) staining is a well-known approach to identify overexpression of proteins on cells in pathology tissue slides. The staining results in a typical brown appearance of tissue where the targeted protein is overexpressed as compared to normal. For example, by using an antibody against programmed death ligand 1 (PD-L1), its overexpression can be detected. The result is typically indicated as a so-called proportionality score, i.e. the percentage of tumor cells that are designated as positive (above threshold).

3D images can be obtained from the biopsy or resected tissue material, with or without staining, in order to provide an intermediate 3D representation of the morphology of the biopsy before processing in paraffin and micro-toming into thin microscopy sections for pathology image acquisition. This can be done for example by optical coherence tomography, X-ray, and or multifocal microscopy after clearance of the tissue with an index matching substance.

The detection of features in pathology slides may be performed using known computer algorithms which can analyse digital images of the slides. For instance, convolutional neural networks may be trained by providing annotated data sets of pathology images where the objects of interest have been annotated manually by a pathologist. Such objects can be for instance cell nuclei. Also the classification of cell nuclei into for instance tumor cells or immune cells can be trained successfully. Thus in particular embodiments, deep learning computer algorithms may be trained and/or used to detect cell nuclei on digital images of tissue, and even discriminate between tumor and non-tumor tissue.

Computer-based detection algorithms may also be used in combination with IHC to detect cells of interest (e.g. overexpressing a particular protein) automatically. For instance, the presence and abundance of cells that are classified as being positive for the overexpression of PD-L1 in IHC images can be determined. Using computer-based detection enables true quantification of the number and density of objects in a region of interest, like a tumor lesion.

Figure 3:
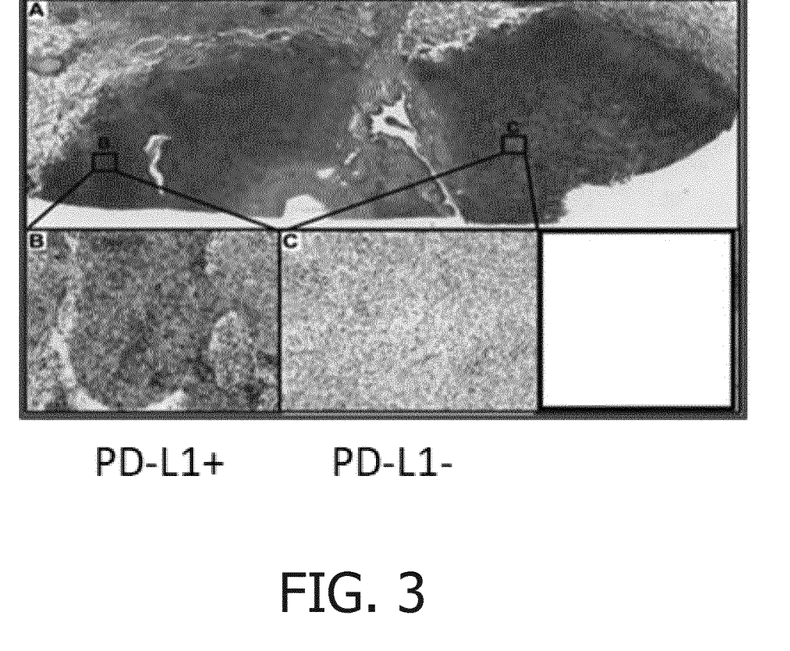
FIG. 3 shows a pathology image of a biopsy sample from a tumor stained for PD-L1 expression. (A) shows a low resolution image of stained sample, indicating regions B and C. (B) shows a high resolution image of region B, which is PD-L1 positive (i.e. shows elevated PD-L1 expression). (C) shows a high resolution image of region C, which is PD-L1 negative.

In a preferred embodiment, the biological parameter detected in the biopsy sample is PD-L1 expression. PD-L1 is a cell membrane protein, one of the so-called checkpoint molecules, important for the communication between tumor and immune cells. It may also be considered to be a signature of increased metabolic activity of the tumor cells. PD-L1 expression on tumor cells can be constitutive (mutation-driven) or induced (via immune challenge). PD-L1 expression is typically determined with an immunohistochemical staining assay on tissue slides. Several commercial assays are available (see e.g. F. R. Hirsch et al., J. Thorac. Onc., 12, 208). PD-L1 overexpression on tumor and in some cases immune cells is used as a diagnostic test to guide the therapy selection. For instance advanced lung cancer patients that have a score of more than 50% PD-L1 positive tumor cells are eligible for checkpoint inhibition monotherapy, while patients with a lower score will qualify for a combination of checkpoint inhibition and chemotherapy. It is known that the expression of PD-L1 can be heterogeneous within a lesion and between lesions in a patient. An example of a tissue section from a tumor biopsy stained for PD-L1 is shown in FIG. 3, indicating regions of widely varying PD-L1 expression.

In one embodiment, described herein is a method of obtaining a score for the representativeness of a biopsy from a tumor based on an analysis of radiology images, in particular FDG-PET/CT. The method may comprise the following steps:
1. Acquire a (FDG-)PET/CT image of a tumor lesion;
2. Analyse the PET image:

a. Define a region of interest (contour of the lesion of choice);
 b. Determine a parameter related to metabolic activity (e.g. SUV) in the area of interest;
 c. Calculate contour plots of iso-parametric volumes;
 d. Calculate a volume percentage of the lesion with parameter above a threshold;
3. Calculate a score reflecting the probability of obtaining a biopsy that would represent the part of the lesion above the threshold value;
4. Report the score to the radiologist, and/or pathologist and/or treating physician
5. Optionally indicate if the score is below a predefined value.

In one embodiment the volume percentage (step 2.d) can be calculated based on a minimum connected volume with a value above a threshold. The volume can be defined in relation to the volume of a core biopsy sample. The threshold values can be related to the volume average value or by the maximum in the particular volume element.

In another embodiment no threshold is used in step (2.d), but instead the probability (step 3) is calculated of having a biopsy volume removed with a parameter score that is equal or higher than the volume average of the total lesion.

In another embodiment the local activity parameter as derived from the local PET SUV value can be corrected by a local parameter obtained from a CT image of the same location that would reflect the tissue density. This correction can be performed by e.g. dividing the SUV value by a density parameter. In another embodiment, the local parameter reflecting the tissue density can be determined by an appropriate MR sequence.

If the biopsy location is known and can be registered to the radiology image, the probability of a biopsy being representative can be calculated with higher precision by calculating the volume fraction having the same or higher value as the average of the local biopsy volume element. If the biopsy location can be registered perfectly to the radiology image, then the value of the biological parameter obtained from the biopsy should correspond to the tumor activity value at that location, assuming that the biological parameter and tumor activity show a known correlation. Typically the biopsy volume is of the same order of magnitude as the resolution of the radiology (e.g. PET) image. Therefore if the heterogeneity score indicates that a high volume fraction of the tumor exceeds the predetermined threshold of tumor activity, biopsy samples taken from most locations within the tumor would be expected to show a value of the biological parameter above a corresponding clinically relevant threshold thereof. If however the value of the biological parameter obtained from the biopsy is negative (i.e. below the clinically relevant threshold) despite a high volume fraction of the tumor being above the predetermined tumor activity threshold obtained via radiology, this discordance is indicative that the value of the biological parameter may be unrepresentative of the tumor.

The contour plots as well as the probability of a biopsy being representative can be provided to the radiologist or nuclear medicine physician, e.g. on a display. The same information can also be reported to the pathologist to take into consideration when performing the pathological scoring, as well as to the treating physician. For instance a risk score derived from the probability can be displayed to the radiologist, and/or pathologist and/or treating physician.

In a preferred embodiment, the contour plot can be used to guide the biopsy towards the location with the largest connected volume having a parameter value above threshold.

In another embodiment, a local heterogeneity of the parameter can be calculated for the lesion, and optionally displayed in an augmented radiology image. The local heterogeneity can be correlated to histopathological parameters. This can be performed for all lesions in a patient with multiple lesions. In this way it is possible to define an interlesion heterogeneity parameter.

The threshold value (2.d) can be predetermined e.g. from cohort studies, and optionally adjusted to the specific patient image acquisition conditions.

In one embodiment, FDG-PET and SUV is used for correlation with PD-L1 expression in pathology. The steps of one such non-limiting embodiment are set out below.

Figure 4:
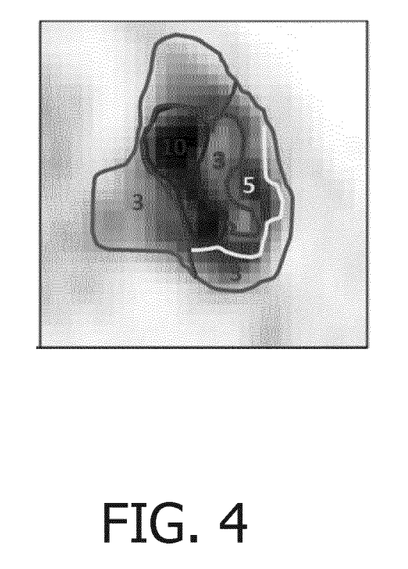
FIG. 4 shows a PET image of a tumor, which features a contour plot in which the solid lines indicate regions of the tumor having equal values of metabolic activity (SUV). Volume regions of the tumor with a SUV higher than 10, with an SUV between 5 and 10, and with an SUV between 3 and 5 are thus indicated.
Figure 5:
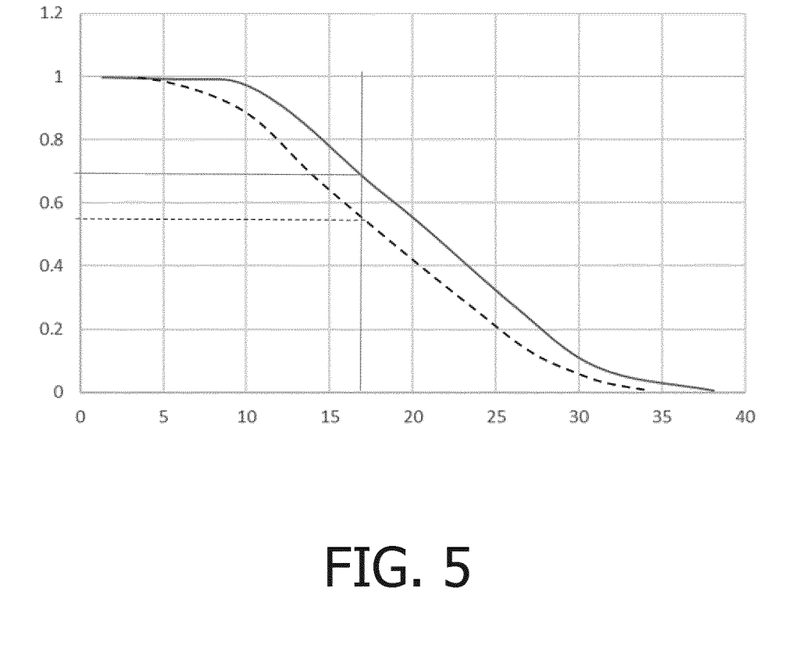
FIG. 5 shows an SUV histogram of volume elements from a region of interest. Solid line per voxel, broken line per analysis volume (corresponding to the biopsy volume). The vertical line indicates a preselected threshold value for a corresponding pathological interpretation. The cut point indicates the fraction of volume elements that would have an SUV lower than the threshold. For a larger volume element (i.e. a biopsy volume) that fraction would be smaller, as indicated by the broken line.

An FDG-PET/CT image is acquired according to well-known clinical procedures and instruments. In the first step after image acquisition and standard image corrections and post-processing, the lesion volume is defined as contours in the 3D image. The SUV is calculated for each voxel in the image of the lesion. Volume elements of equal SUV values are determined and indicated by iso-SUV contour lines in the image for predetermined (binned) SUV values. A contour plot showing volume elements of equal SUV values is shown in e.g. FIG. 4. Restrictions can be applied to the minimum size of the volume element for which the such created sub-volumes (minimum island size, granularity) are indicated. In addition a histogram of the SUV distribution can be generated and a heterogeneity score can be calculated therefrom, e.g. as shown in FIG. 5.

A predetermined threshold value of SUV, which is relevant for the correlation to a pathology parameter (for example the PD-L1 expression on tumor cells), can be selected and indicated in the histogram, and optionally all volume elements with an SUV equal or higher than the threshold value can be highlighted in the image. The volume fraction of the total lesion having an SUV value above the threshold can be indicated as a score. This score relates to the unbiased probability of extracting a sample by a biopsy procedure that is characterized by an SUV value above threshold.

Both the volume fraction of the lesion above threshold as well as the location of the volume elements above threshold are reported.

This information can be used to indicate to a clinician to guide the biopsy needle to a region with the highest SUV value and a connected volume significantly larger than the biopsy volume to be removed, if such an area is accessible. If not, the best alternative region can be selected to which the biopsy is guided. At the same time, a fraction of the volume expected to be above threshold in the biopsy sample is calculated.

In the case of an uninformed biopsy, the information concerning the volume fraction above threshold (i.e. heterogeneity score) is reported to the pathologist. The pathologist (optionally using an automated image analysis system) may have determined a score of the PD-L1 expression on tumor cells as a percentage of positive tumor cells (tumor proportion score or TPS). In case this score is negative or below 50% this has consequences for the care path to be selected for the patient. In cases where the TPS is below a threshold, and the volume fraction above SUV threshold in the PET image is relatively high (e.g. above 20%, the discordance between the TPS and SUV indicating a risk of a non-representative result), the TPS score can be flagged as a potential false negative (or false below the 50% threshold). Re-biopsy can be advised based on such a result. If this is not acceptable, the risk of having a false negative PD-L1 score can be reported to the clinician and taken into account when the therapy is selected.

The present method uses a predetermined threshold of tumor activity values obtained from the radiological image to determine the heterogeneity score. Since the tumor activity parameter (e.g. based on SUV) correlates with the biological parameter (e.g. PD-L1 score), a clinically relevant threshold for the biological parameter can be used to calculate the predetermined threshold of tumor activity. As long as the relationship between the clinically relevant threshold of the biological parameter and the predetermined threshold of tumor activity is known (e.g. regardless of whether the correlation is linear or non-linear), it is possible to translate the threshold for e.g. 1% and 50% TPS into corresponding SUV thresholds by a simple correlation equation that can be obtained from a one-time experimental correlation curve. The relationship between e.g. SUV obtained by FDG-PET and PD-L1 expression is known (see e.g. Zhou et al. (2018), Eur J Nucl Med Mol Imaging 45 (Suppl 1):S441, EP-0367).

In a preferred embodiment a correlation function is used to relate the predetermined threshold for the heterogeneity determination to a clinically relevant threshold of the biological parameter. In other words, the correlation function allows an appropriate predetermined threshold of the tumor activity value (e.g. an SUV) to be selected, based on a known cut-off value of the biological parameter that provides a diagnostic or clinical indication (e.g. a threshold of TPS that indicates suitability for checkpoint inhibitor therapy).

The correlation function relates the local biological parameter from pathology with the calculated local radiology signal. In one example the biological parameter is the percentage of PD-L1 positive tumor cells in a tissue area and the tumor activity is determined as the local SUV from an FDG-PET image. For a clinical question a particular PD-L1 positive tumor cell percentage (so-called tumor proportion score, TPS) is of relevance. From the correlation function the corresponding SUV value can be derived when a clinical cut-off is selected.

For checkpoint immunotherapy of advanced lung cancer patients with pembrolizumab a cut off of 50% TPS is used. Therefore the corresponding SUV value for 50% TPS is selected as a threshold for the calculation of the tumor heterogeneity. For the treatment with a combination of pembrolizumab with chemotherapy a cut-off of 1% TPS is used. In this case a different threshold for the SUV is selected for the calculation of the tumor heterogeneity. Consequently, the reported tumor heterogeneity and corresponding risk of having a non-relevant biopsy result depends on the clinical threshold of the biological parameter that is involved. For the same patient the heterogeneity score is different for the 1% TPS and the 50% TPS. In general a higher TPS threshold will lead to a higher corresponding predetermined threshold of the SUV, and thus a smaller volume fraction of the tumor lesion with an SUV value equal or higher than the predetermined threshold. The heterogeneity score determined using the two different thresholds will vary accordingly.

The methods, systems, and devices discussed above are examples. Various configurations may omit, substitute, or add various procedures or components as appropriate. For instance, in alternative configurations, the methods may be performed in an order different from that described, and that various steps may be added, omitted, or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Embodiments of the present disclosure, for example, are described above with reference to block diagrams and/or operational illustrations of methods, systems, and computer program products according to embodiments of the present disclosure. The functions/acts noted in the blocks may occur out of the order as shown in any flowchart. For example, two blocks shown in succession may in fact be executed substantially concurrent or the blocks may sometimes be executed in the reverse order, depending upon the functionality/acts involved. Additionally, or alternatively, not all of the blocks shown in any flowchart need to be performed and/or executed. For example, if a given flowchart has five blocks containing functions/acts, it may be the case that only three of the five blocks are performed and/or executed. In this example, any of the three of the five blocks may be performed and/or executed.

Specific details are given in the description to provide a thorough understanding of example configurations (including implementations). However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the spirit or scope of the disclosure.

Having described several example configurations, various modifications, alternative constructions, and equivalents may be used without departing from the spirit of the disclosure. For example, the above elements may be components of a larger system, wherein other rules may take precedence over or otherwise modify the application of various implementations or techniques of the present disclosure. Also, a number of steps may be undertaken before, during, or after the above elements are considered.

Having been provided with the description and illustration of the present application, one skilled in the art may envision variations, modifications, and alternate embodiments falling within the general inventive concept discussed in this application that do not depart from the scope of the following claims.

Features of some arrangements are set out in the following numbered paragraphs:

1. A computer-implemented method (200) for determining tumor heterogeneity, the method comprising:
    analyzing (202) a radiological image of a tumor to calculate a value indicative of tumor activity at each of a plurality of locations in the tumor;
    determining (204) whether each calculated value is above a predetermined threshold; and
    calculating (206) a heterogeneity score for the tumor; wherein the heterogeneity score is calculated based on a volume fraction of the tumor having a value indicative of tumor activity above the predetermined threshold.
2. A method according to paragraph 1, further comprising calculating (208) a probability of a biopsy sample obtained from the tumor having a value of tumor activity above the predetermined threshold, wherein the probability is calculated based on the heterogeneity score and a volume of the biopsy sample.

3. A method according to any preceding paragraph, wherein the predetermined threshold of tumor activity is correlated with a clinically relevant threshold of a biological parameter associated with the tumor.

4. A method according to paragraph 3, wherein the biological parameter comprises an expression level of programmed death-ligand 1 (PD-L1) on tumor cells.

5. A method according to paragraph 3 or paragraph 4, wherein the clinically relevant threshold of the biological parameter is a percentage of tumor cells positive for PD-L1 expression (TPS) indicative of suitability for checkpoint inhibition therapy.

6. A method according to any preceding paragraph, further comprising comparing the heterogeneity score with a value of the biological parameter determined from a biopsy sample obtained from the tumor; wherein a discordance between the heterogeneity score and the value of the biological parameter is indicative that the value of the biological parameter is unrepresentative of the tumor.

7. A method according to paragraph 6, wherein if the heterogeneity score indicates a significant volume fraction of the tumor has a value indicative of tumor activity above the predetermined threshold, and the value of the biological parameter is below a clinically relevant threshold, the method further comprises indicating the value of the biological parameter as a potential false negative result.

8. A method according to any preceding paragraph, wherein the radiological image is obtained by positron emission tomography (PET), magnetic resonance imaging (MRI), computerized tomography (CT) and/or single-photon emission computed tomography (SPECT), or any combination thereof.

9. A method according to paragraph 8, wherein the value indicative of tumor activity in the tissue is a standard uptake value (SUV) obtained from PET imaging.

10. A method according to paragraph 9, wherein the value indicative of tumor activity is obtained by PET imaging using (18-F) fluorodeoxyglucose (FDG).

11. A method according to any preceding paragraph, further comprising calculating a contour plot showing regions of the tumor having equal values of tumor activity, wherein a contour in the contour plot corresponds to the predetermined threshold of tumor activity.

12. A method according to any preceding paragraph, further comprising indicating to a user a region of the tumor having tumor activity above a predetermined threshold from which a biopsy sample is to be extracted.

13. A method according to any preceding paragraph, wherein the volume fraction of the tumor is determined based on a minimum connected volume with a value above the predetermined threshold.

14. A method according to any preceding paragraph, wherein the value indicative of tumor activity is indicative of metabolic activity, hypoxia, tumour activation of signalling pathways and/or proliferation in the tumor.

15. A system (100) for determining tumor heterogeneity, the system comprising: an interface (110) for receiving a radiological image of a tumor;
a memory (106); and a processor (104) configured to execute instructions stored on the memory to:
(a) analyze the radiological image of the tumor to calculate a value indicative of tumor activity at each of a plurality of locations in the tumor;
(b) determine whether each calculated value is above a predetermined threshold; and
(c) calculate a heterogeneity score for the tumor; wherein the heterogeneity score is calculated based on a volume fraction of the tumor having a value indicative of tumor activity above the predetermined threshold.

16. A computer program product comprising a non-transitory computer readable medium, the computer readable medium having computer readable code embodied therein, the computer readable code being configured such that, on execution by a suitable computer or processor, the computer or processor is caused to perform the method of any of paragraphs 1 to 14.

The invention claimed is:

1. A computer-implemented method for determining representativeness of a pathology score to a tumor, the method comprising:

analyzing a radiological image of a tumor to calculate a value indicative of tumor activity at each of a plurality of locations in the tumor;

determining whether each calculated value at each of the plurality of locations in the tumor is above a predetermined threshold to identify the total number of calculated values above the predetermined threshold;

calculating a heterogeneity score for the tumor, wherein the heterogeneity score is calculated based on a volume fraction of the tumor having a value indicative of tumor activity above the predetermined threshold, and thus wherein the heterogeneity score is calculated by dividing the total number of calculated values above the predetermined threshold by a total number of locations in the tumor for which a calculated value was determined; and calculating a probability of a biopsy sample obtained from the tumor having a value of tumor activity above the predetermined threshold, wherein the probability is calculated based on the heterogeneity score and a volume of the biopsy sample.

2. A method according to claim 1, wherein the predetermined threshold of tumor activity is correlated with a clinically relevant threshold of a biological parameter associated with the tumor.

3. A method according to claim 2, wherein the biological parameter comprises an expression level of programmed death-ligand 1 (PD-L1) on tumor cells.

4. A method according to claim 2, wherein the clinically relevant threshold of the biological parameter is a percentage of tumor cells positive for PD-L1 expression (TPS) indicative of suitability for checkpoint inhibition therapy.

5. A method according to claim 1, further comprising comparing the heterogeneity score with a value of the biological parameter determined from a biopsy sample obtained from the tumor; wherein a discordance between the heterogeneity score and the value of the biological parameter is indicative that the value of the biological parameter is unrepresentative of the tumor.

6. A method according to claim 5, wherein if the heterogeneity score indicates a significant volume fraction of the tumor has a value indicative of tumor activity above the predetermined threshold, and the value of the biological parameter is below a clinically relevant threshold, the method further comprises indicating the value of the biological parameter as a potential false negative result.

7. A method according to claim 1, wherein the radiological image is obtained by positron emission tomography (PET), magnetic resonance imaging (MRI), computerized tomography (CT) and/or single-photon emission computed tomography (SPECT), or any combination thereof.

8. A method according to claim 7, wherein the value indicative of tumor activity in the tissue is a standard uptake value (SUV) obtained from PET imaging.

9. A method according to claim 8, wherein the value indicative of tumor activity is obtained by PET imaging using (18-F) fluorodeoxyglucose (FDG).

10. A method according to claim 1, further comprising calculating a contour plot showing regions of the tumor having equal values of tumor activity, wherein a contour in the contour plot corresponds to the predetermined threshold of tumor activity.

11. A method according to claim 1, further comprising indicating to a user a region of the tumor having tumor activity above a predetermined threshold from which a biopsy sample is to be extracted.

12. A method according to claim 1, wherein the volume fraction of the tumor is determined based on a minimum connected volume with a value above the predetermined threshold.

13. A method according to claim 1, wherein the value indicative of tumor activity is indicative of metabolic activity, hypoxia, tumour activation of signalling pathways and/or proliferation in the tumor.

14. A system for determining representativeness of a pathology score to a tumor, the system comprising:
   an interface for receiving a radiological image of a tumor;
   a memory; and
   a processor configured to execute instructions stored on the memory to:
      (a) analyze the radiological image of the tumor to calculate a value indicative of tumor activity at each of a plurality of locations in the tumor;
      (b) determine whether each calculated value at each of the plurality of locations in the tumor is above a predetermined threshold to identify the total number of calculated values above the predetermined threshold;
      (c) calculate a heterogeneity score for the tumor, wherein the heterogeneity score is calculated based on a volume fraction of the tumor having a value indicative of tumor activity above the predetermined threshold, and thus wherein the heterogeneity score is calculated by dividing the total number of calculated values above the predetermined threshold by a total number of locations in the tumor for which a calculated value was determined; and
      (d) calculate a probability of a biopsy sample obtained from the tumor having a value of tumor activity above the predetermined threshold, wherein the probability is calculated based on the heterogeneity score and a volume of the biopsy sample.

15. A computer program product comprising a non-transitory computer readable medium, the computer readable medium having computer readable code embodied therein, the computer readable code being configured such that, on execution by a suitable computer or processor, the computer or processor is caused to perform the method of claim 1.

* * * * *